United States Patent [19]

Lloyd

[11] Patent Number: 5,073,487
[45] Date of Patent: Dec. 17, 1991

[54] RAPID ASSAY FOR FUNCTIONAL HUMAN $\alpha_1$-PROTEINASE INHIBITOR

[75] Inventor: Cynthia A. Lloyd, Athens, Ga.

[73] Assignee: Athens Research and Technology, Inc., Athens, Ga.

[21] Appl. No.: 303,904

[22] Filed: Jan. 30, 1989

[51] Int. Cl.$^5$ .............................................. C12Q 1/37
[52] U.S. Cl. ........................................ 435/23; 435/4; 435/13; 435/24; 435/19; 530/380; 530/392; 530/829; 530/830
[58] Field of Search ................... 435/4, 13, 23, 24, 19; 530/380, 392, 829, 830

[56] References Cited

U.S. PATENT DOCUMENTS 4,493,891  1/1985  Travis .................................... 435/23

OTHER PUBLICATIONS

Bjork et al. (1985), Biochemistry, vol. 24, ppo. 2653–2660.
Feldman, et al., Proc. Natl. Acad. Sci., 82, 5700–5704 (Sep. 1985).
Gaillard et al., J. Clin. Chem. Biochem., 26, 167–172 (1987).
Hubbard et al., JAMA, 1259–64 (1988).

Primary Examiner—Robert A. Wax
Assistant Examiner—Ardin H. Marschel
Attorney, Agent, or Firm—Kilpatrick & Cody

[57]  ABSTRACT

A simple, rapid and reliable assay for measuring functional enzyme inhibitor levels in body fluids and tissues, especially functional $\alpha_1$-proteinase inhibitor levels in human plasma or serum. $\alpha_2$-Macroglobulin is first inactivated, then porcine pancreatic elastase incubated with the samples to form a complex between the elastase and the functional $\alpha_1$-PI. Deficient individuals are detected by the presence of a color change following addition of substrate. If desirable, residual enzyme activity can then be calculated and the $\alpha_1$-PI levels present in the original sample determined. The method provides a means for early screening of individuals with a genetic deficiency in circulating levels of $\alpha_1$-PI, thereby facilitating treatment and prevention of familial emphysema.

17 Claims, No Drawings

RAPID ASSAY FOR FUNCTIONAL HUMAN $\alpha_1$-PROTEINASE INHIBITOR

The U.S. government has rights in this invention by virtue of Grant Number 1 R43 HL40770 from the National Heart, Lung, and Blood Institute.

This invention relates to a highly selective method for measuring functional $\alpha_1$-proteinase inhibitor levels to aid in the diagnosis of familial emphysema.

Familial emphysema is an inherited disease which develops as a result of proteinase-proteinase inhibitor imbalance in the lung due to insufficient production of the plasma protein referred to as $\alpha_1$-proteinase inhibitor ("$\alpha_1$-PI") or $\alpha_1$-antitrypsin. The $\alpha_1$-PI fraction normally neutralizes the antiproteolytic effects of leukocyte proteolytic enzymes released during an inflammatory response.

Some individuals, however, have an autosomal recessive gene disorder which severely diminishes the $\alpha_1$-PI activity in the lower respiratory tract, and can develop emphysema even without exposure to substances known to cause lung disease. This genetic disorder is particularly common in northern Europe. Diagnosis of the disorder is not normally made until the patient has developed some type of irreversible respiratory insufficiency, primarily because testing, a twenty-four hour isoelectricfocusing procedure, is not a routine procedure in most clinical laboratories or physicians' offices. As a result, most individuals with abnormally low circulating levels of functional $\alpha_1$-PI, referred to as having genotype ZZ, are unknowingly at risk of developing emphysema, particularly if they smoke or are exposed to environmental hazards. $\alpha_1$-PI levels in plasma can be measured using immunochemical methods or functional assays. Immunochemical assays for $\alpha_1$-PI that are currently available include radial immunodiffusion, electroimmuno assays and automated nephelometric assays. Unfortunately, these methods have limited usefulness do not distinguish active from inactive $\alpha_1$-PI.

Functional assays, which measure inhibition of porcine pancreatic elastase (PPE) by $\alpha_1$-PI, are usually based on cleavage of synthetic substrates, including N-tert-butoxycarbonyl-L-alanine-p-nitrophenyl-ester and N-succinyl-L-alanyl-L-alanyl-L-alanine-p-nitroanilide, by residual elastase. The disadvantage of these assays is that $\alpha_2$-macroglobulin is present in plasma and also inhibits elastase, thereby interfering with $\alpha_1$-PI inhibition. These enzyme complexes are still able to hydrolyze small amounts of synthetic substrates. Functional assays such as those described by Gaillard and Kilroe-Smith, "Determination of Functional Activity of $\alpha_1$-Protease Inhibitor and $\alpha_1$-Macroglobulin in Human Plasma Using Elastase," *Clin. Chem. Clin. Biochem.* 25, 167-72 (1987), measure the functional levels of both the $\alpha_1$-PI component and the $\alpha_1$-Macroglobulin, which obscures the clinical usefulness of the test.

A method for assaying for inactive $\alpha_1$-PI is disclosed by U.S. Pat. No. 4,493,891 to Travis. This method is based on the quantitation of oxidized $\alpha_1$-PI in serum or plasma by comparing inhibition of porcine pancreatic elastase with inhibition of trypsin-like enzymes. When $\alpha_1$-PI is oxidized, it loses the ability to inhibit the elastase but not the trypsin-like enzymes.

As in the functional assays for $\alpha_1$-PI, however, the presence of $\alpha_1$-Macroglobulin ("$\alpha_2$-M") in the sample interferes with the measurement of functional $\alpha_1$-PI in serum or plasma.

A simple, highly selective assay for the early screening of individuals for $\alpha_1$-PI deficiency could result in a significant reduction in the number of cases of familial emphysema which develop as a result of this proteinase-proteinase inhibitor imbalance.

It is therefore an object of the present invention to provide a simple and rapid assay for the measurement of functional $\alpha_1$-PI in plasma cr serum.

It is a further object of the present invention to provide an assay for functional $\alpha_1$-PI in plasma or serum which can be used to detect carriers of the gene resulting in defective $\alpha_1$-PI.

It is a still further object of the present invention to provide an assay for functional $\alpha_1$-PI in plasma or serum which eliminates background substrate hydrolysis resulting from $\alpha_2$-Macroglobulin-elastase complexes.

SUMMARY OF THE INVENTION

A simple, rapid and reliable assay for measuring functional enzyme inhibitor levels in body fluids and tissues, especially functional $\alpha_1$-proteinase inhibitor levels in human plasma or serum is disclosed. $\alpha_2$-Macroglobulin is first inactivated, then porcine pancreatic elastase incubated with the samples to form a complex between the elastase and the functional $\alpha_1$-PI. Deficient individuals are detected by the presence of a color change following addition of substrate. If desirable, residual enzyme activity can then be calculated and the $\alpha_1$-PI levels present in the original sample determined. The method provides a means for early screening of individuals with a genetic deficiency in circulating levels of $\alpha_1$-PI, thereby facilitating treatment and prevention of familial emphysema.

DETAILED DESCRIPTION OF THE INVENTION

The method described below with respect to $\alpha_1$-PI can be used as an assay to measure any functional non $\alpha_2$-macroglobulin inhibitor of an enzyme inhibited by $\alpha_2$-macroglobulin, such as elastase, trypsir, cathepsin G, chymotrypsin, thrombin, and plasmin, in a sample derived from blood, lymph, synovial fluid, or tissue. $\alpha_2$-M is a glycoprotein present in human plasma at a concentration of 1.5-4.2 g per liter which is capable of binding to serine, cysteine, metallo, and carboxyl proteases. The "bait region" of this inhibitor is a specific sequence of amino acids which may be cleaved by one of these proteases, leading to a conformational change in the inhibitor that causes the protease to become trapped by the inhibitor, as reviewed by Feldman et.al., "Model of $\alpha_2$-Macroglobulin Structure and Function," *Proc. Natl. Acad. Sci. USA* 85, 5700-04 (1985).

However, even though the trapped protease exhibits little or no activity toward native proteins, it still possesses catalytic activity toward low molecular weight substrates. A problem can therefore arise when low molecular weight substrates are used to measure the protease inhibitory capacity of human plasma, specifically in reference to $\alpha_1$-PI activity. Unlike neutrophil elastase, complexes of $\alpha_2$-M with pancreatic elastase do not show increased esterase activity toward specific synthetic substrates. This difference is rendered moot, however, when the $\alpha_2$-M in the plasma samples is inactivated, as described below.

The method includes the steps of (1) inactivating the $\alpha_2$-macroglobulin in the sample using a specific inhibitor such as a hydrazine, ammonium sulfate, or acyl, alkyl, or aromatic amine, which does not inactivate the enzyme inhibitor to be measured, (2) adding substrate specific for the enzyme which will produce an easily detectable color change if cleaved by the enzyme to be measured, and (3) providing the enzyme in a known quantity. The enzyme can be isolated from tissue or body fluids, or a product of genetic engineering. If the enzyme is present and functionally active, it will cleave the substrate and a color change will be detected. If the inhibitor is present and functionally active, the enzyme will be inactivated and unable to act upon the substrate.

In the preferred embodiment, the highly selective assay of the present invention for functional $\alpha_1$-proteinase inhibitor ("$\alpha_1$-PI") takes only twenty-five minutes to perform and can be carried out in a 96 well ELISA plate using a total assay volume of 200 µl. If the test is used to quantitate levels of functional enzyme, either the amount of sample (2-10 µl plasma or serum) or elastase (2-10 µg PPE) can be varied to obtain a range of $\alpha_1$-PI activity values.

The procedure is based upon $\alpha_1$-PI inhibition of elastase activity (cleavage of a specific substrate) in a sample following complete inactivation of the $\alpha_2$-M in the sample using a compound which specifically inactivates $\alpha_2$-M and not $\alpha_1$-PI, such as hydrazide, ammonium sulfate, or an acyl, alkyl or aromatic amine like methylamine. Examples of suitable substrates for elastase include low molecular weight substrates that are cleaved by esterases or amidases; nitrophenylesters; $\beta$-napthylamides; aminomethyl coumarin; p-nitroanilides; and succinyl-nitroanilides, as further described by Powers in Methods in Enzymology.

The assay system of the present invention uses the measurement of residual proteinase activity after addition of a given quantity of the enzyme, for example, PPE, to a diluted plasma sample. PPE is complexed in this system only by $\alpha_1$-PI and any free enzyme will be detected by the addition of a specific substrate Sinoe individuals homozygous for the ZZ mutant have only 15% of the normal levels cf $\alpha_1$-PI, it should be easy to detect these patients. It should levels of $\alpha_1$-PI deficiency, as would be found in phenotype MZ individuals.

Early diagnosis of $\alpha_1$-PI deficiency could alert the patient to possible hazards which would exacerbate an emphysematous condition such as cigarette smoking or occupations which involve inhalation of polluted air. This early detection could reduce the number of individuals who develop emphysema and thereby reduce having $\alpha_1$-PI deficiency (ZZ homozygotes) could benefit from plasma $\alpha_1$-PI infusions, soon to be commercially available from Cutter Laboratories, or from infusions of an elastase inhibitor, several of which are now in testing.

The present invention is further illustrated by the following nonlimiting examples.

EXAMPLE 1

Preparation and Optimization of Reagents for use in $\alpha_1$-PI Assay

A. Purification of $\alpha_1$-Proteinase Inhibitor $\alpha_1$-PI is purified from 8 units (approximately 1800 ml) of whole human plasma. The 50–80% $(NH_4)_2SO_4$ precipitate is collected via centrifugation at 16,300 X g for 15 minutes, dialyzed against 0.03 M sodium phosphate, pH 6.5, and then loaded onto a Cibacron TM Blue Sepharose column (CBS, 22×3.5 cm) equilibrated with the same buffer. Unbound material is collected and loaded onto a DE-52 column (22×3.5 cm) also equilibrated with 0.03 M sodium phosphate, pH 6.5. The DE-52 column is washed with at least two bed volumes of buffer to remove any unbound material. A one liter gradient (0–0.2 M NaCl in 0.03 M phosphate buffer, pH 6.5) is applied to the column. Fractions possessing $\alpha_1$-PI inhibitory activity are pooled.

Purity is determined by gel electrophoresis on 8% sodium dodecyl sulphate ("SDS") nonreducing polyacrylamide gels, and by immunodiffusion using the method of Ouchterloney, or by other methods known to those skilled in the art. About 250 mg of purified $\alpha_1$-PI is obtained from one liter of whole human plasma B. Purification of Porcine Pancreatic Elastase Twice crystallized PPE was purified from 500 g of trypsin 1–300 (ICN Biochemicals, Cleveland, OH) using the procedure of Shotten, Methods in Enzymology vol. 19, 113 (1970).

Five hundred grams of trypsin 1–300 is stirred with 2500 ml of 0.1 M sodium acetate buffer, pH 4.5, for 3 hours, and then centrifuged at 16,300 X g for 15 minutes. The supernatant is saved and the pellet reextracted with an additional 2000 ml of the acetate buffer, and spun as before. The two supernatants are pooled and the insoluble residue discarded. The combined extract is brought to 45% saturation with solid ammonium sulfate. After stirring for 30 minutes the precipitate is removed by centrifugation at 16,300 X g for 30 minutes. The precipitate is suspended three times using an electric blender with 1000 ml of the acetate buffer saturated to 45% with ammonium sulfate. The supernatant is discarded each time.

The washed ammonium sulfate precipitate is dissolved in 2000 ml of 0.05 M $Na_2CO_3$-HCl buffer, pH 8.8, and dialyzed against four changes of 20 liters of distilled water for 48 hours to remove all salt. The euglobulin precipitate is removed by certrifugation and washed twice with 1000 ml distilled water. The supernatant and washings are discarded.

The precipitate is suspended in 2000 ml of 0.02 M Tris base and dissolved by adjusting the pH to 10.4 with 1 M NaOH. The pH is then brought to pH 9.4 with 1 M HCl and the solution stirred with about 1500 ml settled bed volume of DEAE-Sephacel TM which has previously been equilibrated with 0.02 M Tris-HCl, pH 8.8. After 4 hours, the suspension is filtered under gentle vacuum and washed with an additional 1000 ml of 0.02 M Tris-HCl, pH 8.8. The combined filtrate is brought to pH 5.0 with glacial acetic acid, dialyzed overnight against three changes of 20 liters of 1 mM acetic acid, and lyophilized using standard techniques.

The lyophilized powder is dissolved in 0.01 M sodium acetate buffer, pH 5.0, to a final protein concentration of about 25 mg per ml. One molar sodium sulfate is slowly added to the redissolved powder with stirring to a final concentration of 0.1 M sodium sulfate. After about 24 hours, the resulting elastase crystals are filtered on a sintered glass funnel and washed twice with 20 ml of 1.2 M sodium sulfate, buffered at pH 5.0 with 0.01 M sodium acetate. The crystals are then suspended in 1000 ml cf distilled water, completely redissolved by dialysis against three changes of 20 liters of 1 mM acetic acid, and lyophilized. The crystallization procedure is repeated to give twice crystallized elastase.

EXAMPLE 2

Enzyme Activity Assays and Inactivation of $\alpha_2$-M with Appropriate Inhibitor

Trypsin Active Site Titration

The activity of porcine pancreatic trypsin, obtained from Sigma Chemical Co., St. Louis, MO, is titrated using 10 mM p-nitrophenyl p-guanidiobenzoate HCl ("NPGB") in dimethyl sulfoxide ("DMSO"), according to the method of Chase and Shaw, *Biochem. Biophys. Res. Commun.* 29, 508–524 (1967). 0.6–3.0 mg of trypsin are dissolved in 3.0 ml barbitone-calcium buffer (100 mM sodium barbitone, 20 mM calcium chloride, adjusted to pH 8.3 with concentrated HCl before dilution to full volume). Thirty microliters of NPGB stock (3.37 mg NPGB/ml DMSO, stored at 4° C.) is added to a tube with the trypsin at time zero. The change in absorbance at 410 nm is used to determine the concentration of trypsin, assuming that one molecule of trypsin hydrolyses one molecule of NPGB. Active site titrated trypsin used in these studies was 72% active, based on the commercially available trypsin consisting of 94% protein by weight.

B. Standardization of $\alpha_1$PI Activity

Zero to 20 µg of purified $\alpha_1$-PI is incubated with 6 µg of trypsin in 2 ml 0.1 M Tris-HCl buffer, pH 8.1. Fifty microliters of benzoyl-arginine L-nitroanilide (40 mg per ml in DMSO, stored at 4° C.) is added to each tube at timed intervals so start the reaction, and the tubes incubated at room temperature for 10 minutes. The reaction is stopped by the addition of 1 ml of 5 M formate, pH 3.0, and the absorbance at 410 nm recorded. Assays are run in triplicate and $\alpha_1$-PI activity extrapolated from a curve drawn correlating % trypsin inhibition to the weight amount of $\alpha_1$-PI present, knowing the amount of active site titrated trypsin used for the assay. $\alpha_1$-PI used in this study was 83% active.

C. PPE Activity

Zero to 16 µg $\alpha_1$-PI were incubated with 8 µg of PPE in 970 µl of 0.2 M Tris, pH 8.0, for 5 minutes. Thirty microliters of succinyl-L-ala-ala-ala-p-nitroanilide (suc-triala-p-NA) 28.2 mg per ml dimethylformamide) is added and the reaction followed spectrophotometrically at 410 nm for 1 minute. Assays are run in triplicate and PPE activity extrapolated from a curve drawn correlating % PPE inhibition to the titrated amount of $\alpha_1$-PI present, knowing the amount of PPE used in the assay. Four µg (2.9 µg active) PPE is the preferred amount for use in the assay. PPE in this study was 72.5% active.

Zero to 20 µg of PPE (30 µl) is added to 920 µl of phosphate buffered saline (PBS, pH 7.2), fifty microliters of tert-butoxycarbonyl-L-alanine-p-nitrophenyl ester substrate (t-boc-ala-NP, 31.1 mg in 10 ml acetonitrile) is added and the change in absorbance at 347.5 nm is monitored for 1 minute.

D. $\alpha_2$-M Activity

Two to 40 µg of $\alpha_2$-M is incubated with 4 µg of elastase in a volume of 970 µl 1 0.2 M Tris, pH 8.0, for 5 minutes at room temperature. Ten µg of $\alpha_1$-PI is added to inactivate the uncomplexed PIE and the mixture incubated at room temperature for an additional 5 minutes. Thirty microliters of suctriala-p-NA is added and the mixture is incubated at room temperature for 20 minutes more. The reaction is stopped by the addition of 150 µl of 0.5 M citric acid.

E. Inactivation of $\alpha_2$-M with Methylamine

To inactivate the $\alpha_2$-M in a sample of plasma, 50 µl of a stock solution of 4 M methylamire in 0.2 M Tris-HCl pH 8.0 is added to 1 ml of the sample. The sample is then allowed to react at 25° C. for a specific time, one hour or less.

Example 3

Adaption of Assay for Clinical Application

The assays described in the following studies for $\alpha_1$-PI and $\alpha_2$-M have been adapted to 200 µl volumes for use in 96 well ELISA plates, and are readily adapted to clinical application.

A. Choice of Enzyme $\alpha_1$-PI is able to inactivate pancreatic trypsin even though control of neutrophil elastase activity is believed to be the physiological function of this inhibitor. Porcine pancreatic trypsin and PPE are both inactivated by $\alpha_1$-PI. PPE is inactivated only by native $\alpha_1$-PI and $\alpha_2$-M, although complexes with $\alpha_2$-M can still hydrolyze small synthetic substrates. Since the association rate for $\alpha_2$-M and PPE is 10 times slower than that for PPE and $\alpha_1$-PI, 90% of the complex formation should theoretically occur with $\alpha_1$-PI and 10% with $\alpha_2$-M if saturating amounts of enzyme are used.

PPE does not form complexes with oxidized $\alpha_1$-PI, and therefore one may obtain a true measurement of functional inhibitor. Trypsin is able to react with oxidized $\alpha_1$-PI at a slower rate, although oxidized $\alpha_1$-PI is nonfunctional in terms of its ability to control the activity of neutrophil elastase. Because trypsin can interact with other inhibitors in plasma, which would present an additional source of error, PPE is the enzyme of choice for the assay for $\alpha_1$-PI.

B. Choice of Substrate

The criteria in determining the appropriate substrate are specificity and sensitivity to the enzyme to be measured, cost, and extent of background hydrolysis. Background substrate hydrolysis is undesirable in an assay which depends upon visual inspection of a paper strip or an ELISA plate. These factors can be determined and evaluated using methods known to those skilled in the art, as demonstrated below

1. T-boc-ala-NP

Two substrates were tested for use in the $\alpha_1$-PI assay. The first was the simple ester substrate tert-butoxycarbonyl-L-alanine-p-nitrophenyl ester (t-boc-ala-NP, 31.1 mg in 10 ml acetonitrile). The advantage of this substrate is its low cost. 30 µl of PPE (0 to 20 µg) was added to 920 µl of phosphate buffered saline (PBS, pH 7.2). 50 µl of t-boc-ala-NP was added per tube and the change in absorbance at 347.5 nm was monitored for 1 min using a Varian DMS 200 spectrophotometer. When the assay was performed using 10 µl of plasma and no PPE there was a substantial amount of background substrate hydrolysis, about 0.04 optical density units per min.

2. suc-triala-p-NA $\alpha_1$-PI (0 to 16 µg) or plasma (0 to 10 µl) was incubated with PPE (0 to 10 µg) in a final volume of 970 µl of 0.2 M Tris, pH 8.0, for 5 min. 30 μl succinyl-L-ala-ala-ala-p-nitroanilide (suc-triala-p-NA, 28.2 mg per ml dimethylformamide) was added and the reaction followed spectrophotometrically at 410 nm for 1 min. This substrate was determined to be more suitable than t-boc-ala-NP because of its stability and sensitivity. Further, the product of elastase hydrolysis of suc-triala-p-NA, p-nitroaniline, can be converted to a stable and even more sensitive diazo dye.

The suc-triala-p-NA substrate was also shown to be much more sensitive than the t-boc-ala-NP substrate, since the t-boc-ala-NP required about twice the amount of PPE to elicit an optical density change equivalent to the change observed when using the suctriala-p-NA substrate under similar assay conditions.

C. Inactivation of $\alpha_2$-M by Methylamine

The effectiveness of adding an inactivator of $\alpha_2$-M to the sample prior to determining $\alpha_1$-PI inhibitory activity has been demonstrated using the inactivator methylamine.

The $\alpha_2$-M activity was measured as described above. Briefly, after incubating 4 μg of PPE with increasing amounts of $\alpha_2$-M, without the prior addition of methylamine, the excess PPE was inactivated by adding a two fold excess of $\alpha_1$-PI over that required to inhibit the PPE. At higher levels of $\alpha_2$-M there was increased elastase activity, probably because of the ability of this enzyme trapped by $\alpha_2$-M to cleave small molecular weight substrates, as indicated by an increase in absorbance at 410 nm.

When the $\alpha_2$-M is inactivated by addition of methylamine immediately before the assay, the inactivated $\alpha_2$-M is not able to trap the PPE. The excess $\alpha_1$-PI is therefore able to inactivate all of the PPE.

To ascertain the effect of methylamine on $\alpha_1$-PI, increasing amounts of purified $\alpha_1$-PI, incubated with and without methylamine for 1 hour, were incubated with 4 μg PPE and the mixture was allowed to sit at room temperature for 5 minutes. Thirty microliters of suc-triala-p-NA substrate was added and the reaction was allowed to proceed for 10 minutes. The reaction was terminated as before, and the tubes read at 410 nm. These data indicate that methylamine does not affect $\alpha_1$-PI activity under these conditions.

Various molar ratios of $\alpha_1$-PI and $\alpha_2$-M were titrated against 2.88 μg of PPE (4 μg weight, 72% active) Unreacted PPE was inactivated using a two fold excess of $\alpha_1$-PI and the assay completed as described above. Titration of increasing amounts of each $\alpha_1$-PI/$\alpha_2$-M mixture resulted in a biphasic curve. The initial linear negative regression may be attributed to $\alpha_1$-PI inhibitory activity, while the increase in PPE activity represented in the later part of the curve results from substrate hydrolysis by PPE trapped by $\alpha_2$-M. This occurs because the relative amount of PPE bound to $\alpha_2$-M increased as the total amount of mixture used in the assay increased. As the relative amount of $\alpha_1$-PI was decreased, the volume corresponding to that required for maximum inhibition increased from 2.5 to 30.8 μl, with a concomitant fifteen fold increase in absorbance.

For purposes of comparison, the same study was conducted using $\alpha_1$-PI/$\alpha_2$-M mixtures inactivated with methylamine prior to assay. The curves obtained for all mixtures indicate that since the $\alpha_2$-M has been inactivated, only $\alpha_1$-PI remains to inactivate PPE, resulting in a simple single component curve. Accordingly, inactivation of the $\alpha_2$-M prior to assaying is preferred.

EXAMPLE 4

Rapid Clinical Assay for functional $\alpha_1$-PI

The preferred embodiment of the $\alpha_1$-PI assay protocol is as follows. All steps are performed at room temperature (25° C.). pH adjustment of the plasma sample was found not to be crucial to the inactivation of $\alpha_2$-M by methylamine.

The $\alpha_2$-M in the plasma sample to be tested is inactivated by adding 50 μl of 4 M methylaxine (in 0.2 M Tris pH 8.0) to a 1 ml plasma sample, and allowing the sample to sit for 15 minutes. Porcine pancreatic elastase ("PPE") and plasma are added to a volume of 0.2 M Tris pH 8.0 in a microtiter plate well to a final volume of 100 μl. PPE and plasma are incubated together for 5 minutes so that the enzyme can bind to the inhibitor. Fifty microliters of substrate (succinyl-L-ala-ala-ala-p-nitroanilide, 1.27 mg suc-triala-p-NA/ml 0.2 M Tris pH 8.0) is added to the reaction mixture and allowed to incubate for 5 minutes. The reaction is stopped by the addition of 50 μl of 0.5 M citric acid, and the color of the sample solutions determined using a Titertek TM Uniskan plate reader at 410 nm or by visual inspection.

Modifications and variations of the present invention, a highly selective method for measuring functional enzyme inhibitor levels, especially $\alpha_1$-proteinase inhibitor levels, in human fluids and tissue, will be apparent to those skilled in the art from the foregoing detailed description. Such modifications and variations are intended to be included within the scope of the following claims.

I claim:

1. A method for detecting the presence of functional non $\alpha_2$-macroglobulin inhibitors of enzymes that are inhibited by $\alpha_2$-macroglobulin in a sample derived from human tissue or fluids comprising providing in an assay:
   a specific inactivator of $\alpha_2$-macroglobulin and not of the inhibitor to be detected;
   a specific substrate for an enzyme that is inhibited by $\alpha_2$-macroglobulin and by the inhibitor to be detected, wherein the substrate results in a detectable product when reacted;
   the enzyme in a known quantity; and
   the sample to be assayed for the presence of inhibitor other than $\alpha_2$-macroglobulin.

2. The method of claim 1 wherein the enzyme is selected from the group of active enzymes consisting of elastase, trypsin, cathepsin G, chymotrypsin, thrombin, and plasmin.

3. The method of claim 1 wherein the non $\alpha_2$-M inhibitor is $\alpha_1$-proteinase inhibitor.

4. The method of claim 1 wherein the inactivator is selected from the group of specific inactivators of $\alpha_2$-macroglobulin consisting of hydrazines, ammonium sulfate, and alkyl and aromatic amines, which do not inactivate the enzyme inhibitor to be measured.

5. The method of claim 4 wherein the inactivator is methylamine.

6. The method of claim 1 wherein the substate is a low molecular weight compound yielding a chromogenic or fluorogenic product selected from the group of substates cleaved by esterases and amidases consisting of nitrophenylesters, β napthylamides, aminomethyl coumarin, p-nitroanilides, and succinyl-nitroanilides.

7. The method of claim 6 wherein the inhibitor is $\alpha_1$-proteinase inhibitor, the enzyme is elastase, and the substate is selected from the group consisting of tertbutoxycarbonyl-L-alanine-p-nitrophenyl ester and succinyl-L-ala-ala-ala-p-nitroanilide.

8. The method of claim 1 wherein the sample is selected from the group consisting of blood, plasma, serum, lymph, synovial fluid, and tissue.

9. The method of claim 2 further comprising determining whether the enzyme cleaves the added substrate.

10. An assay for determining the presence of functional non $\alpha_2$-macroglobulin inhibitors of enzymes that are inhibited by $\alpha_2$-macroglobulin in a sample derived from human tissue or fluids comprising in an assay:
- a specific inactivator of $\alpha_2$-macroglobulin and not of the inhibitor to be determined;
- a specific substrate for an enzyme that is inhibited by $\alpha_2$-macroglobulin and by the inhibitor to be detected that results in a detectable product when cleaved;
- the enzyme in a known quantity; and
- the sample to be assayed for the presence of inhibitor other than $\alpha_2$-macroglobulin.

11. The assay of claim 10 further comprising functional enzyme that is inhibited by the inhibitor to be detected.

12. The assay of claim 11 wherein the enzyme is selected from the group of active enzymes consisting of elastase, trypsin, cathepsin G, chymotrypsin, thrombin, and plasmin.

13. The assay of claim 12 wherein the non $\alpha_2$-inhibitor is $\alpha_1$-proteinase inhibitor.

14. The assay of claim 12 wherein the inactivator is selected from the group of specific inactivators of $\alpha_2$-macroglobulin consisting of hydrazines, ammonium sulfate, and alkyl and aromatic amines, which do not inactivate the enzyme inhibitor to be measured.

15. The assay of claim 13 wherein the inactivator is methylamine.

16. The assay of claim 12 wherein the substate is a low molecular weight compound yielding a chromogenic or fluorogenic product selected from the group of substrates cleaved by esterases and amidases from the group of substates cleaved by esterasesand amidases consisting of nitrophenylesters, $\beta$ napthylamides, aminomethyl coumarin, p-nitroamilides, and succinylnitroanilides.

17. The assay of claim 15 wherein the inhibitor is $\alpha_1$-proteinase inhibitor, the enzyme is elastase, the inactivator is methylamine and the substrate is selected from the group consisting of tert-butoxycarbonyl-L-alanine-p-nitrophenyl ester and succinyl-L-ala-ala-ala-p-nitroanilide.

* * * * *